United States Patent [19]
Winston et al.

[11] Patent Number: 5,318,773
[45] Date of Patent: * Jun. 7, 1994

[54] ANTICALCULUS DENTIFRICES

[75] Inventors: Anthony E. Winston, East Brunswick; Regina M. Miskewitz, Hillsborough; Darlene R. Walley, Princeton; John R. Berschied, Lawrenceville, all of N.J.

[73] Assignee: Church & Dwight Co., Inc., Princeton, N.J.

[*] Notice: The portion of the term of this patent subsequent to Jan. 19, 2010 has been disclaimed.

[21] Appl. No.: 5,626

[22] Filed: Jan. 19, 1993

Related U.S. Application Data

[63] Continuation of Ser. No. 753,340, Aug. 30, 1991, Pat. No. 5,180,576.

[51] Int. Cl.$^5$ .......................... A61K 7/16; A61K 7/18
[52] U.S. Cl. ........................................ 424/52; 424/49; 424/57
[58] Field of Search ..................................... 427/49-58

[56] References Cited

U.S. PATENT DOCUMENTS 5,180,576 1/1993 Winston et al. .................. 424/52

Primary Examiner—Shep K. Rose
Attorney, Agent, or Firm—Charles B. Barris

[57] ABSTRACT

Dentrifices, including toothpastes or dental creams, gels and tooth powders, incorporating alkali metal pyrophosphate salts and sodium bicarbonate in amounts effective to inhibit calculus formation on teeth. The sodium bicarbonate improves the calculus inhibiting properties of the pyrophosphate salts, permits the use of smaller quantities of pyrophosphate than required in the absence of the bicarbonate adjuvant, allows the formulation of pyrophosphate containing dentrifices without the need of use unpleasant tasting potassium pyrophosphates to prevent grittiness, and salts-out the pyrophosphate as undisolved tetrasodium pyrophosphate decahydrate in the form of relatively small particles which do not impart a gritty mouth feel upon use of the dentrifice.

32 Claims, No Drawings

ANTICALCULUS DENTIFRICES

This is a continuation of application Ser. No. 07/753,340, filed Aug. 39, 1991 now U.S. Pat. No. 5,180,576.

TECHNICAL FIELD

The present invention relates to anticalculus dentifrices, viz., toothpastes, gels and tooth powders, which contain sodium bicarbonate.

BACKGROUND OF THE INVENTION

Calculus, or tartar as it is also referred to, is the solid, hard mass of calcified material deposited on and adherent to the surfaces of the teeth. Calculus is composed of inorganic salts, organic matter and water. The inorganic salts which make the calculus hard and resistant are, as shown by chemical analysis, calcium phosphates, mainly calcium hydroxyapatite, with varying, but small, amounts of other inorganic salts. Although not entirely understood, the general concept is that deposits, mostly plaque, a sticky film of oral bacteria and their products, become calcified with the ultimate formation on teeth of a hard mineral consisting of calcium hydroxyapatite (HAP).

Methods for chemically reducing or preventing calculus formation have been directed at affecting the process at any of several stages in its development. One approach is to develop agents which inhibit the formation of the crystalline calcium phosphate or hydroxyapatite. A chemical agent which would interfere with the crystal growth of hydroxyapatite would be an effective anticalculus agent.

It is well known that dissolved pyrophosphate ions are effective agents in inhibiting the crystal growth of hydroxyapatite. Even at extremely low concentrations, dissolved pyrophosphate is an effective inhibitor of hydroxyapatite formation from its amorphous phases. Draus et al (Arch. Oral Biol. 15: 893–896, 1970) demonstrated that natural pyrophosphate in saliva inhibits the conversion of amorphous calcium phosphate into hydroxyapatite. Their studies, carried out in vitro, suggested that the attachment of pyrophosphate ions to calcium results in a calcium-pyrophosphate complex which causes an inhibition of crystal growth to hydroxyapatite. Draus et al were also aware of the presence of pyrophosphatase in the saliva of subjects who were calculus formers and pointed out that pyrophosphate ions or complexes can be hydrolyzed by the enzyme to form orthophosphate ions or calcium orthophosphate which are inactive as inhibitors of hydroxyapatite formations. They suggested that dissolved pyrophosphate ions would inhibit calculus formation if the pyrophosphate could be protected from pyrophosphatase-induced hydrolysis. (For example, it has been known for some time that fluoride ion is a pyrophosphatase inhibitor. Rapp et al, J. Dent. Res. 39: 372–376, 1960; Vogel et al, Archs. Oral Biol. 12: 159–163, 1967.)

Briner et al (W. W. Briner, M. D. Francis, "In Vitro and In Vivo Evaluation of Anti-Calculus Agents". Calc. Tiss. Res. 11:10–22 (1973)) demonstrated the in vitro and in vivo anticalculus effects of dissolved pyrophosphate ions and showed that 1% solutions applied to the teeth of rats could reduce calculus severity by 38.2% and incidence by 11.7%.

In the light of these disclosures, Parran et al, in U.S. Pat. Nos. 4,515,772, 4,590,066, 4,684,518, 4,806,339, 4,885,155 and 4,999,184, have proposed as anticalculus agent dentifrices and mouthwashes containing mixtures of various alkali metal pyrophosphate salts and soluble fluorides. Parran et al claimed that those compositions capable of providing at least 1.5% of dissolved $P_2O_7^{-4}$ ions were effective in reducing calculus.

The efficacy of dentifrices containing pyrophosphate ions and sodium fluoride in preventing calculus deposits has been confirmed in many published clinical studies. For example, Lobene (Clinical Preventive Dentistry 8(3):5–7, 1986) showed that the use of a dentifrice theoretically containing 3.3% pyrophosphate ion (from 5.0% tetrasodium pyrophosphate) and 0.243% sodium fluoride resulted in a 44.2% reduction in calculus deposits after three months when compared to a placebo dentifrice containing 0.243% sodium fluoride without pyrophosphate ions. Using a dentifrice containing a similar concentration of pyrophosphate ion, Schiff (Clinical Preventative Dentistry 9(2) 13–16 (1987)) obtained a 35.5% reduction after three months and a 45.95% reduction after six months.

It has been found, however, that dentifrice compositions containing high proportions of tetrasodium pyrophosphate as the anticalculus agent, especially in the amounts used above, e.g., 5% tetrasodium pyrophosphate by weight, are gritty, and that the solid gritty particles are composed of undissolved tetrasodium pyrophosphate species. While the gritty particles in such dentifrices can be avoided by employing a predominant portion of the pyrophosphate in the form of the tetrapotassium salt, see, for example, Gaffar et al, U.S. Pat. Nos. 4,806,340 and 4,931,273, problems still exist with these compositions due to the objectionable taste of the tetrapotassium salts when used in large amounts.

It has also been proposed to add synthetic anionic polymeric polycarboxylate salts to pyrophosphate/fluoride-containing anticalculus dentifrices to further inhibit phosphatase-induced hydrolysis of pyrophosphate ions or the calcium-pyrophosphate complex formed therefrom. Thus, Gaffar et al U.S. Pat. Nos. 4,627,977, 4,806,342 and 4,869,898 disclose such formulations containing as little as 0.1% pyrophosphate, but exemplifying only formulations containing 3%, 6% and 7% by weight of tetrasodium pyrophosphate. Gaffar et al U.S. Pat. Nos. 4,806,340, 4,906,456, 4,925,654, 4,931,273 and 4,966,777 disclose the use of from 4.3% to 7% of alkali metal pyrophosphate as an anticalculus agent, at least 4.3% of which is tetrapotassium pyrophosphate and up to 2.7% of which is tetrasodium pyrophosphate. Finally, Gaffar et al U.S. Pat. No. 4,889,712 discloses the use of pyrophosphate ion in amounts below 3% by weight when it is admixed with the polycarboxylate salt in proportions of from about 0.3:1 to about 2.5:1.

The anticalculus efficacy of dentifrices containing low levels of pyrophosphate in combination with polymeric polycarboxylate was confirmed by Singh et al. (J. Clin. Dent. 2:53–55, 1990) and by Schiff et al. (J. Clin. Dent. 2:48–52, 1990). In these clinical studies the effect on calculus deposits of dentifrices theoretically containing 1.3% pyrophosphate ion (from 2.0% tetrasodium pyrophosphate)? either alone or in admixture with 1.5% of a copolymer of methoxyethylene and maleic acid, was studied. It was found that the dentifrices containing both the soluble pyrophosphate and the carboxylate copolymer additive significantly reduced supragingival calculus formation after an initial oral prophylaxis, to the extent of about 29% to 36% in excess of the results obtained by use of placebo dentifrices absent such materials. On the other hand, it was concluded that dentifrices containing 1.3% soluble pyrophosphate but no carboxylate copolymer did not significantly reduce supragingival calculus formation.

One problem with the addition of carboxylate copolymers to dentifrices, however, is that many people find the slick feeling on the teeth and in the mouth, due to the presence of polymer residue after brushing, to be unpleasant.

Accordingly, in spite of the many disclosures dealing with the use of pyrophosphates as oral anticalculus agents, the need for improved anticalculus dentifrices still exists.

It is among the objects of this invention, therefore, to provide improved anticalculus dentifrices which will not be subject to one or more of the above problems and disadvantages.

Other objects and advantages will appear as the description proceeds.

SUMMARY OF THE INVENTION

In accordance with the present invention, it has been found that the addition of sodium bicarbonate to an alkali metal pyrophosphate-containing, anticalculus dentifrice imparts improved calculus-inhibiting properties thereto. Moreover, dentifrices containing the bicarbonate/pyrophosphate anticalculus mixtures of the invention may be formulated without the noticeable presence of high proportions of undesirably gritty tetrasodium pyrophosphate particles, without the need for the addition of potassium pyrophosphates which can impart an objectionable taste, and without the unpleasant mouth feel of dentifrices containing polycarboxylate salts. In contrast to the addition of high molecular weight carboxylate polymers or copolymers, the addition of sodium bicarbonate imparts a very fresh clean feeling to the teeth and mouth after brushing.

The dentifrice compositions of the invention desirably contain about 8 to 95% by weight sodium bicarbonate, about 2.5 to 15% by weight of one or more alkali metal pyrophosphate salts and a fluoride ion source in an amount sufficient to supply about 25 to 5,000 ppm fluoride ion. The sodium bicarbonate may act as both a calculus-inhibiting adjuvant and an abrasive in the dentifrice. The bicarbonate may be used alone or in admixture with other dental abrasives, e.g., any of the common water-insoluble dental abrasives known in the art. Moreover, other ingredients conventionally incorporated in dentifrices, e.g. surfactants, flavorants, sweeteners, humectants, thickeners or the like, may additionally be incorporated therein.

In accordance with a preferred embodiment of the invention, the sodium bicarbonate is incorporated in an amount of at least about 20% or more by weight of the dentifrice and the water content of the formulation is between about 5 and 35%. In such compositions, the bicarbonate has a salting-out effect on the alkali metal pyrophosphate, the resulting dentifrice containing no more than about 1.5% dissolved pyrophosphate ion with the remainder of the pyrophosphate salt or salts being converted to solid (undissolved) tetrasodium pyrophosphate decahydrate. Surprisingly, notwithstanding the resulting low proportions of dissolved pyrophosphate ions (cf., the several Parran et al. patents referred to hereinabove), such dentifrice compositions exhibit enhanced anticalculus properties. Moreover, the tetrasodium pyrophosphate decahydrate is salted-out in the form of relatively small particles similar in size or only slightly larger than the particles of sodium bicarbonate used, as distinguished from the relatively large size of the tetrasodium pyrophosphate particles which may form in conventional anticalculus dentifrices utilizing tetrasodium pyrophosphate. Preferably, the tetrasodium pyrophosphate decahydrate is salted out with mean particle sizes within the range of about $20\mu$ to $100\mu$ and with more than 90% of the particles, by count, having a particle size of less than about $20\mu$ in diameter and, preferably, with 90% of the particles, by count, having a particle size of less than about $150\mu$. The small particles of the tetrasodium pyrophosphate decahydrate do not possess the gritty feel previously found objectionable in dentifrice formulations.

Further in accordance with a preferred embodiment of the invention, the pyrophosphates used are added in the form of their sodium salts and the use of potassium salts is avoided. This prevents imparting the unpleasant flavor of potassium salts. Grittiness is avoided as described above.

It has previously been proposed to use sodium bicarbonate in toothpastes or dental creams as an abrasive or polishing agent, or for other purposes. For example, Delaney et al. U.S. Pat. Nos. 3,937,321, 3,937,803, 3,937,804, 3,943,240 and 4,160,022 disclose toothpastes containing sodium bicarbonate as the principal abrasive admixed with a lesser amount of a compatible water-insoluble abrasive. On the other hand, Delaney et al. U.S. Pat. No. 3,935,305 discloses the use of minor amounts of sodium bicarbonate as a secondary abrasive in a dental cream or toothpaste along with major amounts of a water-insoluble abrasive. Delaney et al., however, were not concerned with the inhibition of the formation of hydroxyapatite nor do they teach a method of interfering with the growth thereof by employing an effective anticalculus agent.

Dentifrices containing sodium bicarbonate particles having particular sizes as the sole abrasive, i.e., in amounts greater than 60% by weight, are also described in Winston et al. U.S. Pat. Nos. 4,547,362, 4,623,536, 4,663,153 and 4,721,614, owned by the assignee of the present invention. Winston et al. U.S. Pat. No. 4,943,429 describes tooth gels containing up to 60% sodium bicarbonate, either alone or in combination with secondary abrasives. However, Winston et al. were also not concerned with inhibiting the formation of hydroxyapatite by the use of an effective anticalculus agent.

DETAILED DESCRIPTION OF THE INVENTION

The dentifrices of the present invention include toothpastes or dental creams, dental gels or tooth powders. They comprise the several essential, as well as optional, components disclosed hereinafter.

As indicated hereinabove, sodium bicarbonate is incorporated in the dentifrice formulations as both an anticalculus adjuvant and an abrasive. Desirably, the sodium bicarbonate particles have a mean particle size within the range of about $5\mu$ to $200\mu$, preferably about $20\mu$ to $120\mu$, in diameter. The bicarbonate particles may be incorporated in the dentifrice in varying amounts, depending upon the particular formulation, e.g., tooth powder, toothpaste or gel, so long as it is present in an amount effective to impart the desired abrasive characteristics and to promote inhibition of calculus formation when the dentifrice is applied to the teeth. Accordingly, as used herein, the term "effective" or "effective amount" means a sufficient amount of the ingredient being utilized to provide the desired effect or result. In a dentifrice such as a tooth powder, the amount of sodium bicarbonate required to impart both abrasive and anticalculus adjuvant effects is from about 20% to as much as about 95%.by weight, for a toothpaste or gel preferably from about 8% to 65% by weight. At lower concentrations of bicarbonate the enhancement of anticalculus activity will be small. However, with a concentration of sodium bicarbonate even as low as 8% and a water content of less than about 30%, the noticeable presence of high proportions of gritty tetrasodium pyrophosphate particles will be avoided as described herein.

The soluble pyrophosphate salts which may be incorporated in the dentifrices of the present invention include mono-, di-, tri- or tetra-alkali metal pyrophosphates and mixtures thereof. The preferred pyrophosphate salts include disodium pyrophosphate, tetrasodium pyrophosphate, tetrapotassium pyrophosphate, and mixtures thereof. The pyrophosphates may be employed in their anhydrous as well as their hydrated forms. Although a particular pyrophosphate salt, e.g., disodium pyrophosphate, may be the pyrophosphate initially added to the formulation, the actual pyrophosphate and the quantity present in the product is dependent on both the final pH of the formulation and the salting-out effect of the sodium bicarbonate.

The preferred dentifrice formulations, which contain about 20 to 60% sodium bicarbonate and possess pH values of about 7.5 to 9.5, contain no more than about 1.5%, typically about 0.4–1%, of dissolved pyrophosphate ions, primarily in the form of $HP_2O_7^{-3}$ and $P_2O_7^{-4}$ ions. The balance of the pyrophosphate salt content, e.g. in amounts of about 1.5 to 13.5% by weight of the dentifrice, is in the form of undissolved tetrasodium pyrophosphate decahydrate salted-out by the sodium bicarbonate.

As indicated above, dentifrices containing such sodium bicarbonate/alkali metal pyrophosphate mixtures together with a water soluble fluoride ion source and other conventional dentifrice constituents, exhibit enhanced anticalculus properties. -Such dentifrices may utilize decreased concentrations of total pyrophosphate salts and yet have significant anticalculus activity. Moreover, and quite surprisingly in view of the prior literature, such dentifrices exhibit effective anticalculus activity notwithstanding the fact that they may contain substantially less than 1.5% dissolved pyrophosphate ion and amounts of undissolved tetrasodium pyrophosphate decahydrate in high proportions. Finally, by reason of the salting-out effect of the sodium bicarbonate ingredient, the undissolved tetrasodium pyrophosphate salt is in the form of relatively small particles which do not impart an unpleasant, gritty mouth feel.

As further indicated above, the dentifrices of the invention include a water-soluble fluoride ion source which is effective both as a pyrophosphatase inhibitor and as an anti-caries agent. Fluoride ion sources thus useful include inorganic fluoride salts, such as soluble alkali metal or alkaline earth metal salts, for example, sodium fluoride, potassium fluoride, sodium fluosilicate, ammonium fluosilicate, sodium fluozirconate or sodium monofluorophosphate. Alkali metal fluorides such as sodium fluoride, or sodium monofluorophosphate, and mixtures thereof, are preferred.

The amount of the soluble fluoride ion source in the dentifrice is dependent on the particular compounds used and the type of dentifrice, but it must be incorporated in an effective but nontoxic amount, generally up to about 5.0% of the preparation. Any suitable minimum amount of such compound may be used, but it is preferable to employ a sufficient quantity as to release about 25 up to a maximum of 5,000 ppm, preferably about 850 to 1500 ppm. of fluoride ion. Typically, in the case of sodium fluoride the fluoride ion source is present in an amount from 0.05% to 0.65% by weight, based on the weight of the dentifrice, and preferably in the range of 0.18% to about 0.35%. In the case of sodium monofluorophosphate the compound may be present in an amount of about 0.2–2%, more typically from about 0.65%–1.20%.

The toothpaste, gel or powder vehicle may also contain, if desired, a conventional abrasive or polishing material, in addition to the sodium bicarbonate. Conventional water-insoluble abrasives which are so useful include sodium metaphosphate, potassium metaphosphate, tricalcium phosphate, calcium phosphate dehydrate, anhydrous dicalcium phosphate, calcium pyrophosphate, magnesium orthophosphate, trimagnesium phosphate, calcium carbonate, aluminum silicate, zirconium silicate, hydrated silica, hydrated alumina, bentonite, and mixtures thereof.

Preferred abrasive materials which may be admixed with the sodium bicarbonate include hydrated silica, silica gel or colloidal silica, and complex amorphous alkali metal aluminosilicates. When visually clear gels are employed, polishing agents of hydrated or colloidal silica, alkali metal aluminosilicate complexes and alumina are particularly useful, since they have refractive indices close to the refractive indices of gelling agent-liquid (including water and/or humectant) systems commonly used in such dentifrices.

Any of the foregoing water-insoluble abrasives may be present as an adjunct or secondary abrasive in concentrations of up to about 50%, preferably, in amounts up to about 20%, by weight of the dentifrice.

Organic surface-active agents are used in the dentifrices of the present invention to achieve increased cleaning action, assist in achieving thorough and complete dispersion of the anticalculus agent throughout the oral cavity, and improve the detergent and foaming properties of the dentifrices. Organic surfactants which may be so utilized can be anionic, nonionic or ampholytic in nature.

Examples of suitable anionic surfactants are water-soluble salts of the higher alkyl sulfates, such as sodium lauryl sulfate or other suitable alkyl sulfates having 8 to 18 carbon atoms in the alkyl group, water-soluble salts of higher fatty acid monoglyceride monosulfates, such as the sodium salt of the monosulfated monoglyceride of hydrogenated coconut oil fatty acids, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosinate, and the sodium, potassium, and ethanolamine salts of N-lauroyl, N-myristoyl, or N-palmitoyl sarcosinate which should be substantially free from soap or similar higher fatty acid materials.

Other suitable surface-active materials include nonionic agents such as condensates of sorbitan monostearate with ethylene oxide, condensates of ethylene oxide with propylene oxide or, condensates of propylene glycol (available under the trademark "Pluronics"). Other examples of water-soluble nonionic surfactants useful in the dentifrices of the present invention are the condensation products of ethylene oxide with various other compounds which are reactive therewith and have long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, or polyhydric alcohols (e.g., sorbitan monostearate).

The various surfactants may be utilized alone, or in admixture with one another. In toothpastes, the aggregate amount of the surfactant or surfactants used is preferably within the range of about 0.05% to about 5%, more preferably, from about 0.1% to about 1.0%, by weight.

Suitable flavoring and sweetening agents may also be employed in the dentifrices of the invention. Examples of suitable flavorants include the flavoring oils, for example, oils of spearmint, peppermint, wintergreen, sassafras, clove, sage, eucalyptus, marjoram, cinnamon, lemon and orange, as well as methylsalicylate. Suitable sweeteners include sodium cyclamate, perillartine, saccharin, sodium saccharin and ammoniated glycyrrhizin (e.g., its monoammonium salt), and the like. Suitably, the flavoring and sweetening agent together comprise from about 0.01% to 5% or more by weight of the dentifrice. Preferably, the amount of flavoring oil is above 0.3%, e.g. 0.8 to 1.2%.

Various other materials may be incorporated in the dentifrices of this invention. Examples thereof are coloring and whitening agents, preservatives, silicones, chlorophyll compounds, and mixtures thereof, and other constituents. These adjuvants are incorporated in the instant compositions in amounts which do not substantially adversely affect the properties and characteristics desired and are selected and used in effective amounts, depending upon the particular adjuvant and type of preparation involved.

In a toothpaste, the liquid vehicle may comprise water and humectant, typically in an amount ranging from about 10% to about 90% by weight of the preparation. Glycerine, propylene glycol, sorbitol, polypropylene glycol and/or polyethylene glycol (e.g., molecular weight of 400-600) exemplify suitable humectants/carriers. Also advantageous are liquid mixtures of water, glycerine and sorbitol. In translucent gels, where the refractive index is an important consideration, it is preferred to use higher ratios of humectant to water than in opaque pastes.

Toothpastes, creams and gels typically also contain a natural or synthetic thickener or gelling agent in proportions of about 0.1% to about 10%, preferably about 0.5% to about 5%, by weight. Suitable organic thickeners include sodium carboxymethyl cellulose, gum tragacanth, starch, carrageenan, polyvinylpyrrolidone, hydroxyethylpropyl cellulose, hydroxybutyl methyl cellulose, hydroxypropyl methyl cellulose, or hydroxyethyl cellulose, and are usually used in concentrations of 0.1-2.0%. Inorganic thickeners such as hydrated silicas may also be used at levels of about 0.5-10%.

It is particularly preferred to incorporate the following ingredients in the sodium/alkali metal pyrophosphate-containing, calculus inhibiting tooth pastes or dental creams of the invention.

| Toothpastes or Dental Creams | | |
|---|---|---|
| | Amounts, Percent by Weight (Unless Otherwise Indicated) | |
| Ingredient | Broad Range | Preferred Range |
| Sodium Bicarbonate | 20.00 to 65.00 | 30.00 to 60.00 |
| Pyrophosphate Salt | 2.50 to 15.00 | 2.50 to 5.00 |
| Humectant | 5.00 to 60.00 | 10.00 to 35.00 |
| Organic Thickener | 1.00 to 2.00 | 0.30 to 1.50 |
| Inorganic Thickener | 0.00 to 10.00 | 0.00 to 5.00 |
| Surfactant | 0.05 to 5.00 | 0.10 to 1.00 |
| Water Insoluble Abrasive | 0.00 to 50.00 | 0.00 to 20.00 |
| Sweetener | 0.00 to 10.00 | 0.30 to 2.00 |
| Fluoridating Agent as fluoride ion | 25.00 to 5000 ppm | 850 to 1500 ppm |
| Flavoring Agent | 0.01 to 5.00 | 0.30 to 2.00 |
| Water | 3.00 to 60.00 | 5.00 to 35.00 |

In another particularly preferred embodiment, the following ingredients are incorporated in sodium bicarbonate/alkali metal pyrophosphate-containing, calculus inhibiting dental gels.

| Dental Gels | | |
|---|---|---|
| | Amounts, Percent by Weight (Unless Otherwise Indicated) | |
| Ingredient | Broad Range | Preferred Range |
| Sodium Bicarbonate | 20.00 to 60.00 | 20.00 to 40.00 |
| Pyrophosphate Salt | 2.50 to 15.00 | 2.50 to 5.00 |
| Humectant | 10.00 to 60.00 | 10.00 to 50.00 |
| Organic Thickener | 0.10 to 2.00 | 0.30 to 1.50 |
| Inorganic Thickener | 0.00 to 10.00 | 3.00 to 8.00 |
| Surfactant | 0.00 to 10.00 | 0.30 to 1.00 |
| Water Insoluble Abrasive | 0.00 to 50.00 | 0.00 to 20.00 |
| Sweetener | 0.00 to 10.00 | 0.30 to 2.00 |
| Fluoridating Agent as fluoride ion | 25.00 to 5000 ppm | 850 to 1500 ppm |
| Flavoring Agent | 0.01 to 5.00 | 0.30 to 2.00 |
| Water | 3.00 to 30.00 | 5.00 to 20.00 |

In another preferred embodiment of the invention anticalculus tooth powders comprise the following ingredients:

| Tooth Powders | | |
|---|---|---|
| | Amounts, Percent by Weight (Unless Otherwise Indicated) | |
| Ingredient | Broad Range | Preferred Range |
| Sodium Bicarbonate | 20.00 to 95.00 | 50.00 to 95.00 |
| Pyrophosphate Salt | 2.50 to 15.00 | 2.50 to 5.00 |
| Surfactant | 0.00 to 10.00 | 0.00 to 2.00 |
| Water Insoluble Abrasive | 0.00 to 95.00 | 0.00 to 50.00 |
| Sweetener | 0.00 to 10.00 | 0.30 to 2.00 |
| Fluoridating Agent as fluoride ion | 25.00 to 5000 ppm | 850 to 1500 ppm |
| Flavoring Agent | 0.01 to 5.00 | 0.30 to 2.00 |
| Anti-caking Agent | 0.00 to 5.00 | 0.05 to 0.20 |

The following examples are further illustrative of the present invention, but it is understood that the invention is not limited thereto. All amounts and proportions referred to herein and in the appended claims are by weight and temperatures are in degrees Celsius unless otherwise indicated.

EXAMPLES I AND II—IN VITRO CALCULUS INHIBITION TESTS

These examples demonstrate the in vitro inhibition of hydroxyapatite (HAP) formation by toothpastes of the present invention, as compared with a number of commercially available dentifrices.

To demonstrate and compare the efficacy of toothpastes containing sodium bicarbonate in admixture with alkali metal pyrophosphate salts, the following test and control formulations were prepared:

|  | Examples | | Controls | | |
| --- | --- | --- | --- | --- | --- |
|  | I | II | A | B | C |
| Sodium Bicarbonate | 60.00 | 30.00 | 30.00 | 65.00 | 0.00 |
| Tetrasodium Pyrophosphate | 2.00* | 2.00* | 0.00 | 0.00 | 2.00* |
| Glycerine | 16.08 | 26.00 | 27.00 | 14.58 | 39.50 |
| PEG-8[1] | 1.00 | 2.00 | 2.00 | 1.00 | 5.00 |
| CMC[2] | 0.60 | 1.00 | 1.00 | 0.70 | 1.50 |
| Sodium Fluoride | 0.24 | 0.24 | 0.24 | 0.24 | 0.24 |
| Water | 16.66 | 27.34 | 28.34 | 15.05 | 38.34 |
| Sodium Saccharin | 1.21 | 1.21 | 1.21 | 1.21 | 1.21 |
| Sylodent 700[4] | 0.00 | 7.00 | 7.00 | 0.00 | 7.00 |
| Sylox 2[4] | 0.00 | 1.00 | 1.00 | 0.00 | 3.00 |
| Sodium Lauryl Sulfate | 0.30 | 0.30 | 0.30 | 0.30 | 0.30 |
| Sodium Lauroyl Sarcosinate (30%) | 1.00 | 1.00 | 1.00 | 1.00 | 1.00 |
| Flavor | 0.91 | 0.91 | 0.91 | 0.92 | 0.91 |
|  | 100.00 | 100.00 | 100.00 | 100.00 | 100.00 |

*1.3% pyrophosphate ion
[1]Polyethylene glycol.
[2]Thickener.
[3]Abrasive Hydrated Silica.
[4]Thickening Silica.

The efficacy of the various test and control formulations was evaluated utilizing the pH stat method described in, e.g., *J. Clin, Dent,* 2:48–52 (1990).

Exactly 0.04% of each of the above dentifrices was dissolved in 50 mls of 0.004 molar solutions of disodium hydrogen phosphate at a temperature of 25.0±0.1° C. The pH of the solution was adjusted to pH 7.4 and 2 mls of 0.1 molar calcium chloride at pH 7.4 were added. The resulting precipitation reaction was followed at a constant temperature of 25.0°±0.1° C. by monitoring the quantity of sodium hydroxide necessary to maintain the pH at 7.4 using a pH stat.

The data are presented below:

TABLE I

|  | Inhibition Time |
| --- | --- |
| Example I | 61.0 |
| Example II | 47.5 |
| Control A | 23.75 |
| Control B | 27.5 |
| Control C | 41.25 |
| Control D[1] | 15 |
| Control E[2] | 47.5 |
| Control F[3] | 33.75 |
| Control G[4] | 29.5 |
| No dentifrice | 15.5 |

[1]Regular Crest (Sodium Fluoride, Sorbitol, Water, Hydrated Silica, Trisodium Phosphate, Sodium Phosphate, Xanthan Gum, Carbomer 956, Flavor, Saccharin, Sodium Lauryl Sulfate, Titanium Dioxide, Color)
[2]New Colgate Tartar Control (Sodium Fluoride, Sorbitol, Glycerine, Water, PEG 12, Hydrated Silica, CMC, Flavor, Saccharin, Sodium Lauryl Sulfate, Titanium Dioxide, $Na_4P_2O_7$, PVM/MA Copolymer, Sodium Hydroxide)
[3]Prevent (Sodium Fluoride, Sorbitol, Glycerine, Water, Hydrated Silica, Xanthan Gum, Hydroxyethyl Cellulose, Flavor, Saccharin, Sodium Lauryl Sulfate, Sodium Methylcocoyl Taurate, Titanium Dioxide, Zinc Chloride, Sodium Benzoate, Sodium Gluconate)
[4]Aim Anti-Tartar (Sodium Monofluorophosphate, Sorbitol, Water, Alumina, CMC, Flavor, Saccharin, Sodium Lauryl Sulfate, Titanium Dioxide, Color, Zinc Citrate)

It is apparent from the table that the pastes of Examples I and II, incorporating both sodium bicarbonate and undissolved tetrasodium pyrophosphate decahydrate, inhibited HAP precipitation for markedly larger periods than the pastes incorporating sodium bicarbonate alone (Controls A and B) or tetrasodium pyrophosphate alone (Control C). These two formulations also provided inhibition times which were equal to or better than those achieved with each of the commercial dentifrices.

EXAMPLES III–VI—IN VIVO CALCULUS INHIBITION TESTS

Further demonstrations of the efficacy of formulations of the invention are provided by the results of the following anticalculus tests performed in rats.

The following tooth gel was prepared:

|  | Example III |
| --- | --- |
| Sodium Bicarbonate | 29.000 |
| Tetrapotassium pyrophosphate | 9.400 |
| Glycerin | 14.500 |
| Sorbitol (10% solution) | 20.587 |
| PEG-8 | 1.000 |
| CMC | 0.500 |
| Sodium Fluoride | 0.243 |
| Water | 12.000 |
| Sodium Saccharin | 0.500 |
| Sylodent 700 | 8.000 |
| Sylox 2 | 1.000 |
| Sodium Lauryl Sulfate | 0.500 |
| Sodium Lauroyl Sarcosinate (30%) | 1.670 |
| Flavor | 0.900 |
| Color | 0.200 |

This dentifrice was compared with Regular Crest and Tartar Control Crest in its ability to inhibit calculus formation in rats. The animals in the study (30 per cell) were treated twice daily, five days per week for three weeks. They were provided with Diet I.V. 900 throughout the study. At the completion of the study, the teeth were evaluated for tartar using the method of Francis and Briner (J. Dent. Res. 48:1185–1195 (1969)) with the results shown in Table II. The results shown are reductions in calculus relative to Regular Crest.

TABLE II

| Example III | 32.0% |
| --- | --- |
| Control H (Tartar Control Crest) | 21.0% |

The results indicate the potential superiority of the tooth gel of the invention, containing 29% sodium bicarbonate, over the leading commercial tartar control brand. Both products contained 5% total pyrophosphate ion. However, the tooth gel of the invention contained only 0.82% dissolved pyrophosphate ion with the balance present as tetrasodium pyrophosphate decahydrate. In Control H essentially all of the pyrophosphate was found to be in the dissolved state.

In a second study utilizing a similar protocol, except that treatments were once daily, five days a week for six weeks and ten rats were used per cell, the efficacy of two additional embodiments of the invention was compared with the toothpaste containing sodium bicarbonate without pyrophosphate (Control A), the toothpaste containing pyrophosphate without bicarbonate (Control C), and Regular Crest. These formulations are shown below.

|  | Examples | | Controls | |
| --- | --- | --- | --- | --- |
|  | IV | V | A | C |
| Sodium Bicarbonate | 30.000 | 60.000 | 30.000 | 0.000 |
| Tetrasodium Pyrophosphate | 2.000 | 2.000 | 0.000 | 2.000 |
| Glycerine | 26.000 | 16.083 | 27.000 | 39.500 |
| PEG-8 | 2.000 | 1.000 | 2.000 | 5.000 |
| CMC | 1.000 | 0.600 | 1.000 | 1.500 |
| Sodium Fluoride | 0.243 | 0.243 | 0.240 | 0.243 |
| Water | 27.343 | 16.660 | 28.340 | 38.343 |

-continued

|                                   | Examples |       | Controls |       |
|-----------------------------------|----------|-------|----------|-------|
|                                   | IV       | V     | A        | C     |
| Sodium Saccharin                  | 1.208    | 1.208 | 1.210    | 1.208 |
| Sylodent 700                      | 7.000    | 0.000 | 7.000    | 7.000 |
| Sylox 2                           | 1.000    | 0.000 | 1.000    | 3.000 |
| Sodium Lauryl Sulfate             | 0.300    | 0.300 | 0.300    | 0.300 |
| Sodium Lauroyl Sarcosinate (30% soln) | 1.000 | 1.000 | 1.000    | 1.000 |
| Flavor                            | 0.906    | 0.906 | 0.906    | 0.906 |

It should be noted that Example V is projected to contain about 0.5% pyrophosphate ion in the dissolved state with the balance present as undissolved tetrasodium pyrophosphate decahydrate. The quantity of dissolved pyrophosphate ion in Example IV is estimated to be about 0.8%.

These products were compared with Regular Crest in their ability to inhibit calculus formation in rats:

TABLE III

|              | % Reduction Relative to Water |
|--------------|-------------------------------|
| Example IV   | 26.4%                         |
| Example V    | 43.5%                         |
| Control A    | 13.5%                         |
| Control C    | 29.1%                         |
| Regular Crest| 8.4%                          |

From the preceding it may be seen that the formulation of Example V, containing 60% sodium bicarbonate, exhibits clearly superior calculus inhibition relative to the formulations of Controls A and C. In the case of Example IV, containing a lower level (30%) of sodium bicarbonate and only 0.8% dissolved pyrophosphate ion, calculus inhibition equal to that of Control C, containing no bicarbonate but 1.3% dissolved pyrophosphate ion, was achieved. This result is surprising in view of the Parran et al. disclosures discussed above.

EXAMPLES VI-VIII

Tooth Powders

The following are representative tooth powders of the present invention:

|                          | Example |        |        |
|--------------------------|---------|--------|--------|
|                          | VI      | VII    | VIII   |
| Component                | (Wt. %) | (Wt. %)| (Wt. %)|
| Sodium Bicarbonate       | 91.957  | 89.957 | 82.457 |
| Tetrasodium pyrophosphate| 5.000   | 7.500  | 5.000  |
| Flavor                   | 1.000   | 1.200  | 1.000  |
| Saccharin                | 1.200   | 1.000  | 0.800  |
| Magnesium Oxide          | 0.100   | 0.100  | —      |
| Sodium Fluoride          | 0.243   | 0.243  | 0.243  |
| Sodium Lauryl Sulfate    | 0.500   | —      | 0.500  |
| Sylodent 700             | —       | —      | 10.000 |

What is claimed is:

1. A toothpaste or dental gel for inhibiting calculus formation, said toothpaste or dental gel consisting essentially of, in an orally acceptable vehicle having an aqueous phase,
   (a) at least about 20% by weight of sodium bicarbonate as an anticalculus adjuvant and as a principal abrasive;
   (b) from 2.5 to 15% by weight of one or more undissolved alkali metal pyrophosphate salts;
   (c) no more than 1.5% by weight of pyrophosphate ions dissolved in the aqueous phase of the paste or gel;
   (d) a soluble fluoride ion source sufficient to supply about 25 to 5,000 ppm fluoride ion; and
   (e) 5 to 35% by weight of water, said toothpaste or dental gel being free of undesirably gritty solid undissolved pyrophosphate particles, objectionably tasting tetrapotassium pyrophosphate, and unpleasant slick mouth feeling polymeric polycarboxylate salts.

2. The toothpaste or dental gel of claim 1, wherein contains from 20 to 65% by weight of the sodium bicarbonate.

3. The toothpaste or dental gel of claim 1, wherein the pyrophosphate salt is disodium pyrophosphate, tetrasodium pyrophosphate, tetrapotassium pyrophosphate or mixtures thereof.

4. The toothpaste or dental gel of claim 1, wherein the toothpaste or dental gel contains from about 20 to 60% by weight of sodium bicarbonate and not more than 1.3% dissolved pyrophosphate ion.

5. The toothpaste or dental gel of claim 4, wherein the amount of dissolved pyrophosphate ions is about 0.4–1.0% and wherein the sodium bicarbonate and the alkali metal pyrophosphate salt have particle sizes within the range of $5\infty$ to $200\mu$.

6. The toothpaste of claim 1, wherein the sodium bicarbonate is from 20 to 65% by weight and further consisting essentially of the following ingredients:

| Ingredient             | % by Weight      |
|------------------------|------------------|
| [Sodium Bicarbonate    | 8 to 65]         |
| [Pyrophosphate Salt    | 2.5 to 15.0]     |
| Humectant              | 5 to 60          |
| Organic Thickener      | 1 to 2           |
| Inorganic Thickener    | 0 to 10          |
| Surfactant             | 0.05 to 5.0      |
| Water Insoluble Abrasive | 0 to 50        |
| Sweetener              | 0 to 10          |
| [Soluble Fluoride as fluoride ion | 25 to 5000 ppm] |
| Flavoring Agent        | 0.01 to 5.0      |
| [Water                 | 5 to 60].        |

7. The dental gel of claim 1, wherein the sodium bicarbonate is from 20 to 50% by weight and the water is from 5 to 30% by weight and further consisting essentially of the following ingredients:

| Ingredient             | % by Weight      |
|------------------------|------------------|
| [Sodium Bicarbonate    | 8 to 60]         |
| [Pyrophosphate Salt    | 2.5 to 15.0]     |
| Humectant              | 10 to 60.0       |
| Organic Thickener      | 0.1 to 2.0       |
| Inorganic Thickener    | 0 to 10.0        |
| Surfactant             | 0 to 10.0        |
| Water Insoluble Abrasive | 0 to 50        |
| Sweetener              | 0 to 10          |
| [Soluble Fluoride as fluoride ion | 25 to 5000 ppm] |
| Flavoring Agent        | 0.01 to 5.0      |
| [Water                 | 5 to 30.0].      |

8. The toothpaste or dental gel of claim 1, wherein the undissolved alkali metal pyrophosphate salt is salted out by the sodium bicarbonate in the form of relatively small particles.

9. The toothpaste or dental gel of claim 8, wherein the particles of the salted-out alkali metal pyrophosphate salt are similar in size or only slightly larger than the sodium bicarbonate particles.

10. The toothpaste or dental gel of claim 8, wherein the undissolved alkali metal pyrophosphate salt is tetrasodium pyrophosphate.

11. The toothpaste or dental gel of claim 9, wherein the salt-out alkali metal pyrophosphate salt is tetrasodium pyrophosphate.

12. The toothpaste or dental gel of claim 8, wherein the undissolved alkali metal pyrophosphate salt is tetrasodium pyrophosphate decahydrate.

13. The toothpaste or dental gel of claim 10, wherein the salted-out alkali metal pyrophosphate salt is tetrasodium pyrophosphate decahydrate.

14. The toothpaste of claim 1, wherein the sodium bicarbonate is 20 to 60% by weight and the undissolved alkali metal pyrophosphate salt is tetrasodium pyrophosphate decahydrates, and wherein the sodium bicarbonate and the tetrasodium pyrophosphate decahydrate have particle sizes within the range of $5\infty$ to $200\mu$.

15. The dental gel of claim 1, wherein the sodium bicarbonate is 20 to 60% by weight and the undissolved alkali metal pyrophosphate salt is tetrasodium pyrophosphate decahydrate; and wherein the sodium bicarbonate and the tetrasodium pyrophosphate decahydrate have particle sizes within the range of $5\mu$ to $200\mu$.

16. The toothpaste of claim 14, wherein the particle size is about $20\mu$ to $100\mu$ with more than 90% of the particles having a particle size of less than about $220\mu$ in diameter.

17. The dental gel of claim 15, wherein the particle size is about $20\mu$ to $100\mu$ with more than 90% of the particles having a particle size of less than about $200\mu$ in diameter.

18. The toothpaste of claim 16, wherein more than 90% of the particles have a particle size of less than about $150\mu$.

19. The dental gel of claim 17, wherein more than 90% of the particles have a particles size of less than about $150\mu$.

20. The toothpaste or dental gel of claim 8, wherein the pH is about 7.5 to 9.5.

21. The toothpaste of claim 6, wherein the water insoluble abrasive is up to 50% by weight and is selected from the group consisting of sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, aluminum silicate, zirconium silicate, hydrated silica, hydrated alumina, bentonite and mixtures thereof.

22. The dental gel of claim 7, wherein the water insoluble abrasive is up to 50% by weight and is selected from the group consisting of sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, aluminum silicate, zirconium silicate, hydrated silica, hydrated alumina, bentonite and mixtures thereof.

23. The toothpaste of claim 21, wherein the insoluble abrasive is hydrated silica, silica gel or colloidal silica, and complex amorphous alkali metal aluminosilicates.

24. The toothpaste of claim 22, wherein the insoluble abrasive is hydrated silica, silica gel or colloidal silica, and complex amorphous alkali metal aluminosilicates.

25. The toothpaste of claim 21, wherein the insoluble abrasive is up to 20% by weight.

26. The toothpaste of claim 22, wherein the insoluble abrasive is up to 20% by weight.

27. A toothpaste for inhibiting calculus formation, in an orally acceptable vehicle having an aqueous phase, which consisting essentially of:
    (a) about 17% by weight of water;
    (b) about 60% by weight of sodium bicarbonate as an anticalculus adjuvant and as a principal abrasive;
    (c) about 2% by weight of tetrasodium pyrophosphate salt, with about 1.3% of pyrophosphate ions dissolved in the aqueous phase of the toothpaste and with the remainder of the pyrophosphate salt being undissolved in the aqueous phase of the toothpaste;
    (d) about 0.5% by weight of sodium fluoride;
    (e) up to about 20% by weight of a water-insoluble abrasive;
    (f) about 0.05 to about 5% by weight of one or more surfactants;
    (g) about 0.01 to about 5% by weight of a flavoring and/or a sweetening agent;
    (h) about 0.1 to about 10% by weight of a thickener or a gelling agent; and
    (i) an effective amount of one or more of a coloring and/or a whitening agent, a preservative, a silicone, a chlorophenyl compound, and/or a humectant, with the percentages totaling 100%, the toothpaste being free of undesirably gritty solid undissolved pyrophosphate particles, objectionally tasting tetrapotassium pyrophosphate, and unpleasant slick mouth feeling polymeric polycarboxylate salts.

28. The toothpaste of claim 27, wherein the humectants are about 16% by weight of glycerin and about 1% by weight of polyethylene glycol; wherein the thickener is about 0.6% by weight of carboxymethyl cellulose; wherein the sweetener is about 1.2% by weight of sodium saccharin; wherein the surfactants are about 0.3% by weight of sodium lauroyl sulfate and about 1% by weight of sodium lauroyl sarcosinate (30%); and wherein the flavor is about 0.9% by weight.

29. A toothpaste for inhibiting calculus formation, in an orally acceptable vehicle having an aqueous phase, which consists essentially of:
    (a) about 27% by weight of water;
    (b) about 30% by weight of sodium bicarbonate as an anticalculus adjuvant and as a principal abrasive;
    (c) about 2% by weight of tetrasodium pyrophosphate salt, with about 1.3% of pyrophosphate ions dissolved in the aqueous phase of the toothpaste and with the remainder of the pyrophosphate salt being undissolved in the aqueous phase of the toothpaste;
    (d) about 0.5% by weight of sodium fluoride;
    (e) up to about 20% b y weight of a water-insoluble abrasive;
    (f) about 0.05 to about 5% by weight of one or more surfactants;
    (g) about 0.01 to about 5% by weight of a flavoring and/or a sweetening agent;
    (h) about 0.1 to about 10% by weight of a thickener or a gelling agent; and
    (i) an effective amount of one or more of a coloring and/or a whitening agent, a preservative, a silicone, a chlorophenyl compound, and/or a humectant, with the percentages totaling 100%, the toothpaste being free of undesirably gritty solid undissolved pyrophosphate particles, objectionally tasting tetrapotassium pyrophosphate, and unpleasant slick mouth feeling polymeric polycarboxylate salts.

30. The toothpaste of claim 29, wherein the humectants are about 16% by weight of glycerin and about 2% by weight of polyethylene glycol; wherein the thickener is about 1% by weight of carboxymethyl cellulose; wherein the sweetener is about 1.2% by weight of sodium saccharin; wherein the surfactant are about 0.3% by weight of sodium lauryl sulfate, and about 1% by weight of sodium lauroyl sarcosinate (30%); wherein the water-insoluble abrasive is about 7% by weight of abrasive hydrated silica; wherein the thickener is about 1% by weight of thickening silica; and wherein the flavor is about 0.9% by weight.

31. A dental gel for inhibiting calculus formation, in an orally acceptable vehicle having an aqueous phase, which consists essentially of:
   (a) about 12% by weight of water;
   (b) about 29% by weight of sodium bicarbonate as an anticalculus adjuvant and as a principal abrasive;
   (c) about 9.4% by weight of tetrasodium pyrophosphate salt, with about 0.82% of pyrophosphate ions dissolved in the aqueous phase of the dental gel and with the remainder of the pyrophosphate salt being undissolved in the aqueous phase of the dental gel
   (d) about 0.24% by weight of sodium fluoride;
   (e) about 20% by weight of a water-insoluble abrasive;
   (f) about 0.05 to about 5% by weight of one or more surfactants;
   (g) about 0.01 to about 5% by weight of a flavoring agent and/or a sweetening agent;
   (h) about 0.1 to about 10% by weight of a thickener or a gelling agent; and
   (i) an effective amount of one or more of a coloring and/or a whitening agent, a preservative, a silicone, a chlorophenyl compound, and/or a humectant, with the percentages totaling 100%, the toothpaste being free of undesirably gritty solid undissolved pyrophosphate particles, objectionably testing tetrapotassium pyrophosphate, and unpleasant slick mouth feeling polymeric polycarboxylate salts.

32. The dental gel of claim 31, wherein the humectants are about 14.5% by weight of glycerin, about 20.6% by weight of sorbitol (10% solution), and about 1% by weight of polyethylene glycol; wherein the thickener is about 1% by weight of carboxymethyl cellulose; wherein the sweetener is about 12% by weight of sodium saccharin; wherein the surfactants are about 0.5% by weight of sodium lauryl sulfate and about 1.7% by weight of sodium lauroyl sarcosinate (30%); wherein the water-insoluble abrasive is about 8% by weight of abrasive hydrated silica; wherein the thickener is about 1% by weight of thickening silica; wherein the color is about 0.2% by weight; and wherein the flavor is 0.9% by weight.

* * * * *